United States Patent [19]
Smith et al.

[11] Patent Number: 4,673,754
[45] Date of Patent: Jun. 16, 1987

[54] PLATINUM AND PALLADIUM COMPLEXES

[75] Inventors: Gaylord D. Smith, Ramsey, N.J.; Douglas S. Brown, Tuxedo, N.Y.; Philip Bernstein, Glen Ridge, N.Y.; John E. Weller, Walden, N.Y.

[73] Assignee: Inco Alloys International, Inc., Huntington, W. Va.

[21] Appl. No.: 842,140

[22] Filed: Mar. 21, 1986

Related U.S. Application Data

[60] Division of Ser. No. 540,871, Oct. 14, 1983, which is a continuation-in-part of Ser. No. 440,449, Nov. 10, 1982, abandoned.

[51] Int. Cl.$^4$ ............................................. C07F 15/00
[52] U.S. Cl. ..................................... 556/137; 536/32; 536/51; 536/63; 536/112; 536/121
[58] Field of Search .................. 556/137; 536/51, 112, 536/121, 32, 63

[56] References Cited

U.S. PATENT DOCUMENTS 4,551,502  11/1985  Howell et al. .................. 525/326.9
4,584,392   4/1986  Smith et al. ......................... 556/137

OTHER PUBLICATIONS

Chemical Abstracts V86 64751d, (1976).
Chemical Abstracts V95 199664j, (1981).
Chemical Abstracts V90 48041z, (1978).
Chemical Abstracts V98 34900g, (1982).
Meshnick et al, Antimicrobial Agents & Chemotherapy, 25 (2) 286–288, (1984).
Morris et al, Chem. Biol. Interactions, 7 (1973), pp. 305–315.

*Primary Examiner*—Helen M. S. Sneed
*Attorney, Agent, or Firm*—Raymond J. Kenny; Francis J. Mulligan, Jr.

[57] ABSTRACT

Compositions of matter are provided wherein cis-platinum (II) and cis-palladium (II) moieties having amine substituents are bonded to anionic macromolecular entities. These compositions of matter may have improved solubility in the plasma and are effective antitrypanosomal and antitumor agents in mammals. Alternatively, the compositions of matter may be insoluble in water and particularly adapted for in situ implantation into tumerous masses.

6 Claims, No Drawings

PLATINUM AND PALLADIUM COMPLEXES

This is a divisional of co-pending application Ser. No. 540,871, filed on Oct. 14, 1983, which is a Continuation-In-Part of Ser. No. 440,449, filed on Nov. 10, 1982, now abandoned.

The invention is directed to new compositions of matter containing platinum or palladium and to the use of such compositions of matter in combating cancer cell and trypanosomal infection in mammals

BACKGROUND OF THE INVENTION AND THE PRIOR ART

The compound cisplatin (cis-dichlorodiamine platinum (II)) has become well known in the treatment of various cancers in mammals. The material is toxic and hence can be used only in low dosages. It would be desirable to provide an effective product which could be tolerated in a mammalian body in larger doses and would exhibit a longer half-life. It would also be desirable to provide an effective composition which possessed enhanced solubility in water and serum in comparison to cisplatin. It is to these and other problems that the present invention is directed.

SUMMARY OF THE INVENTION

The invention is directed to the provision of a plurality of cis-platinum or cis-palladium moieties of square-planar coordination about the metal atom (M) in the plus two oxidation state and having the formula (cis M(II)LL')$^{++}$ wherein L and L' is an ammonia or a primary amine, and L and L' can be two primary amine functions on a single molecule, said moiety being bonded to or between two anionic macromolecules having on the average a molecular weight of at least 1,000, e.g., 5,000 to about 60,000. Enzymes having anionic sidechains are included in the expression "anionic macromolecule". The described compositions are adapted to the treatment of mammals infected with inter alia, cancer or trypanosomes.

DETAILED DESCRIPTION OF THE INVENTION

Compositions of matter in accordance with the invention are prepared by reacting an aqueous solution of the anionic macromolecule, which may be in the salt form, e.g., the sodium salt form, with an aqueous solution of an aminated cis-platinum or cis-palladium compound in aquated nitrate form. The platinum or palladium compound may be prepared by the method of Lippert, Lock, Rosenberg and Zvagulis, *Inorganic Chemistry*, Vol. 16, No. 6, 1977, pp. 1525–1529. The reaction mixture is stirred for a considerable time period, e.g., 16 hours or more, and the product is purified by dialysis or filtration, depending upon whether or not the product is soluble in the reaction medium.

The invention is more specifically described as related to compositions of matter comprising initially water soluble organic macromolecular entities having a molecular weight of at least 1000, e.g., about 5000 to about 60,000 and having anionic functional groups thereon whose valence requirements are normally satisfied by a cation from the group of H, NH$_4$, alkali metals, calcium and magnesium characterized in that at least a part of said valence requirements are satisfied by a cationic moiety of square planar coordination having a formula of (cis M(II)LL')$^{++}$ wherein M is either platinum or palladium in the divalent state and L and L' is ammonia or a primary amine. The invention especially concerns the case where L and L' are identical or are two primary amine functional groups present on a single molecule. Representative primary amines which can be used in compositions of the present invention include isomylamine, pentylamine, cyclohexylamine, 1,2-diaminocyclohexane, and ethylenediamine.

The compositions of matter of the present invention are not specific compounds having readily determinable structures, but rather mixtures of related polymeric materials in which a plurality of given square planar platinum or palladium coordination moieties are carried on either one anionic macromolecule or serve as a bridge or bridges between two anionic macromolecules. In cases where multiple bridging occurs, more than two macromolecules can be linked together. In the ordinary case, the compositions of matter of the present invention will contain at least about 2% by weight of platinum or palladium bonded onto the macromolecule (based on metal plus macromolecule weight).

Examples of anionic macromolecular materials which can be employed as the bases for the compositions of matter of the present invention include (but are not limited to) poly-L-glutamic acid (PGA), carboxymethyl cellulose, ferritin, chondroitin sulfate, poly-L-aspartic acid, dextran sulfate, poly[divinyl ether-co-maleic anhydride], poly[acrylic acid co-maleic anhydride], polyacrylic acid, serum albumin and desulfated heparin. More broadly stated, the anionic macromolecules which can be used as the basis of compositions of matter of the present invention are ordinarily anionic polysaccharides, anionic polyamino acids, enzymes having anionic functionality and synthetic macromolecules wherein a sufficient number of repeating units have anionic functionality and optionally other hydrophyllic functional groups to provide water or serum solubility or dispersibility to the synthetic macromolecular substance.

Assuming that the natural or synthetic macromolecular entity employed as a basis for compositions of matter of the present invention is water soluble, it is possible to produce both water-soluble and water-insoluble platinum- or palladium-containing compositions of matter therefrom. As a general rule, if more than about 80% of the free anionic functional groups (e.g., carboxylic acid groups) on a macromolecule are complexed by the (cis MLL')$^{++}$ unit, the resulting composition of matter of the present invention will be insoluble in water or sera owing to both the low solubilizing characteristic of the (cis MLL')$^{++}$ unit compared to say, the sodium ion, and also to the fact that at this high level of precious metal content, the incidence of crosslinking of macromolecules to form even larger macromolecules is inherently high. One must consider the aforestated 80% limit of (cis MLL')$^{++}$ complexing for water- or sera-solubility only as a general rule to which there are a number of exceptions. First, if one selects a very high molecular weight macromolecule to be complexed with the (cis MLL')$^{++}$ unit, such a high molecular weight macromolecule might only tolerate a maximum of say 50% or 60% of its anionic functional units being complexed to provide an end product which is water- or plasma-soluble. Secondly, if the character of the primary amines in (cis MLL')$^{++}$ are such that the R of RNH$_2$ or the R' of NH$_2$R'NH$_2$ is significantly hydrophobic, the macromolecule having anionic functionality will tolerate less complexing by such a (cis MLL')$^{++}$ unit with the final product retaining water-solubility, than it would tolerate where L and L' are $NH_3$ or are the functional groups of $NH_2CH_2CH_2NH_2$.

Thus the compositions of matter of the present invention are divided by character and function into water-soluble species and water-insoluble species. The functions of these so characterized species differ significantly when such compositions are employed as drugs for treating cancers and tumors. The water-soluble species are adapted to be injected into mammalian body fluids, e.g., blood, and, being soluble in the plasma thereof, are adapted to be carried throughout the mammalian body where that fluid flows, absent a biofunctional barrier to the composition of matter. Water-insoluble compositions of the invention on the other hand are readily adaptable to be implanted in tumerous tissue. Such implanted drug compositions can be expected to release relatively high concentrations of therapeutically effective species either by hydrolysis or by minimal solubility or by enzymatic attack or by a combination of all three means in a very local volume thereby directly attacking the cancerous mass.

A number of syntheses are given in the following examples in which the convenient abbreviation (DACH) represents "1,2-diaminocyclohexane," the convenient abbreviation (PGA) represents "polyglutamic acid," and the abbreviation (en) represents "ethylenediamine". In particular, the 1,2-diaminocyclohexane employed in the preparations was obtained from the Aldrich Chemical Co. as an 85% technical grade and comprising a mixture of cis and trans isomers with the trans isomer containing both plus and minus optical enantiomers.

EXAMPLE I

A. Preparation of cis-Pt[(DACH)$H_2O)_2$](NO$_3$)$_2$

Into a 250 mL round bottom flask 16.4 g (0.0431 moles) of pure cis-Pt(DACH)(Cl)$_2$ was charged. A silver nitrate solution was prepared by dissolving 14.34 g (0.0844 moles) of AgNO$_3$ in 100 mLs of distilled water. The solution was then charged into the flask and stirred in the dark at 60° C. for thirty minutes. The suspension was then cooled to room temperature while stirring an additional sixteen hours. Next, the reaction was filtered, resulting in a clear pale yellow aqueous solution containing Pt[(DACH)(H$_2$O)$_2$](NO$_3$)$_2$ solution. Other nitrato platinum (II) and palladium (II) solutions described hereinafter were prepared in a similar manner.

B. Preparation of cis-Pt(DACH) Complexed With Dextran Sulfate

In a 50 mL round bottom flask 0.5 g of dextran sulfate-sodium salt (average molecular weight 5,000) was dissolved in 20 mLs of distilled water. Next, 2.0 mLs of a 0.2615M Pt[(DACH)(H$_2$O)$_2$](NO$_3$)$_2$ aqueous solution prepared as described in 1(A) was slowly added with a syringe to the polymer solution. The reaction was stirred for 16 hours.

The sample was then purified by dialysis over a six hour period (dialysis tubing possessed a molecular weight cut-off of 5,000–6,000). Analysis of the purified sample revealed a 0.19% weight content of platinum in solution. The dialysis product was used in the testing described in Table I.

A portion of the dialysis product was lyophilized to produce a fluffy, crystalline-appearing, golden solid. Lyophilization was accomplished over one week at −60° C., with 10 microns vacuum. The solid product was reconstitutable in distilled water.

EXAMPLE II

Preparation of cis-Pd(DACH) Complexed With PGA

In a 50 mL round bottom flask 1.0 g (0.0066 moles in terms of polymer units) of poly-L-glutamic acid-sodium salt was dissolved in 20 mLs of distilled water. With stirring 14.0 mLs of a 0.1447M cis-Pd[(DACH)(H$_2$O)$_2$](NO$_3$)$_2$ aqueous solution was slowly added with an addition funnel to the polymer solution. The reaction was stirred for 16 hours.

The sample was then purified by dialysis over a sixteen hour period (dialysis tubing possessed a molecular weight cut-off of 6,000). Analysis of the purified sample revealed a 0.22% weight content of palladium in solution.

EXAMPLE III

Preparation of cis-Pt(DACH) Complexed With PGA

In a 50 mL round bottom flask 0.5 g (0.0033 moles in terms of polymer units) of poly-L-glutamic acid-sodium salt (average molecular weight 60,000) was dissolved in 20 mLs of distilled water. With stirring 2.0 mLs of a 0.2615M cisPt[(DACH)(H$_2$O)$_2$](NO$_3$)$_2$ aqueous solution was slowly added with a syringe to the polymer solution. The reaction was stirred for 16 hours.

The sample was then purified by dialysis over a six hour period (dialysis tubing possessed a molecular weight cut-off of 6,000). Analysis of the purified sample revealed a 0.24% weight content of platinum in solution. A portion of the dialysis product was lyophilized as in Example I(B) to produce a fluffy, crystalline-appearing, light-golden solid. Redissolution of the solid in distilled water was accomplished.

EXAMPLE IV

Preparation of cis-Pt(NH$_3$)$_2$ Complexed With PGA

In a 50 mL round bottom flask 1.0 g (0.0066 moles in terms of polymer units) of poly-L-glutamic acid-sodium salt (average molecular weight 60,000) was dissolved in 30 mLs of distilled water. Next, 7.8 mLs of a 0.2537M cis-Pt[(NH$_3$)$_2$(H$_2$O)$_2$](NO$_3$)$_2$ aqueous solution was slowly added with a syringe to the polymer solution. The reaction was stirred for 16 hours.

The sample was then purified by dialysis over a 60 hour period (dialysis tubing possessed a molecular weight cut-off of 5–6,000). Analysis of the purified sample revealed a 0.61% weight content of platinum in solution (24.2% of the free carboxyl side chains on PGA being complexed to platinum).

EXAMPLE V

Cis-Pt(DACH) Complexed With Chondroitin Sulfate

In a 250 mL round bottom flask 2.0 g of chondroitin sulfate-sodium salt was dissolved in 80 mLs of distilled water. With stirring 8.0 mLs of a 0.3405M cis-Pt[(DACH)(H$_2$O)$_2$](NO$_3$)$_2$ aqueous solution was slowly added to the polymer solution. The reaction was stirred for 16 hours. Overnight the reaction product had partially turned to a gel.

The sample was then purified by dialysis over a six hour period (dialysis tubing possessed a molecular weight cut-off of 6,000–8,000). Analysis of the purified sample revealed a 0.455% weight content of platinum in solution.

EXAMPLE VI

Preparation of cis-Pt(NH$_3$)$_2$ Complexed With Bovine Serum Albumin

In a 50 mL round bottom flask 1.0 g of bovine serum albumin (prepared using method IV of Cohn, E. G. et al., *J. Am. Chem. Soc.*, 1947 69 1953) was dissolved in 25 mLs of distilled water. Next, 7.8 mLs of a 0.2537M cis-Pt[(NH$_3$)$_2$(H$_2$O)$_2$](NO$_3$)$_2$ aqueous solution was slowly added with a syringe to the solution of serum albumin. The reaction was stirred for 16 hours.

The sample was then purified by dialysis over a six hour period (dialysis tubing possessed a molecular weight cut-off of 6,000). Analysis of the purified sample revealed a 0.51% weight content of platinum in solution.

EXAMPLE VII

In vivo tests against trypanosomes

In vitro tests against T. Brucei indicated that the compositions cis-Pt(DACH) complexed with (PGA) and cis Pt(NH$_3$)$_2$ complexed with PGA were immediately effective at low dosage levels. Accordingly, in vivo testing was conducted in mice.

The mice selected were NCS male mice weighing 20 to 25 grams. Five animals were used for each dosage level. A count of 50,000 T. Congolense was administered interperitoneally to each animal. At this dosage, control animals given no anti-trypanosomal treatment died in 5 to 8 days. One day after the injection of trypanosomes, the platinum drug of the invention was administered. In one test at 15 mg Pt/kg, cis-Pt(DACH) complexed with (PGA) gave a 20% cure rate; and in another test at 6.25 mg Pt/kg; the same compound gave a 40% cure rate as measured by survival of the animals for 60 days. Other tests with cis-Pt(NH$_3$)$_2$ complexed with (PGA) using four animals per dose gave a 75% cure rate at 20 mg Pt/kg dose and 50% cure rate at 15 mg Pt/kg dose. Mice (four animals per dose level) treated with either 10 mg Pt/kg or 20 mg Pt/kg of cis-Pt(NH$_3$)$_2$ complexed with (PGA) on days 1, 3 and 6 showed cure rates of 100%. After 60 days, blood from surviving animals was administered to other uninfected animals, and no infection resulted. In the testing regime, cisplatin was ineffective at all doses.

EXAMPLE VIII

Various water- and plasma-soluble compounds of the invention were screened for anticancer activity in mice using ascites P388 leukemia cells. The mice were CDF1, female, weighing approximately 20 grams. In each test animal, about $4.8 \times 10^6$ cells were implanted interperitoneally. The test drugs were administered interperitoneally one day after infection. The results are shown in the following Table I.

In Table I the column headed "Log$_{10}$ Change in Tumor Burden at End Rx" means the net log change in viable tumor cell population at the end of the procedure as compared to the start and forms a convenient measure of the order of magnitude of the cell population's change due to treatment. Thus a "−6 log change" means a 99.9999% reduction.

The results achieved as described are considered to demonstrate that compounds produced in accordance with the invention are in many cases more tolerable in mammalian test bodies than the standard cisplatin. It was observed that the composition of cis-Pt(biscyclohexylamine)$_2$ with ferritin, made in manner similar to the procedure described in Example VI, was extremely toxic in mice.

The therapeutic value of certain of the water soluble drugs in trypanosomal treatment is high. It appears that the enhanced solubility characteristics of the compounds will be of great benefit. The degree of solubility and biological parameters can be controlled by varying the total concentration of aminated platinum or palladium complexed to the anionic macromolecules.

The following examples demonstrate the water-insoluble compositions of matter of the present invention.

EXAMPLE IX

One gram of the sodium salt of poly-L-glutamic acid was dissolved in 20 mls of distilled water in a round bottom flask fitted with a magnetic stirrer. To this flask was then slowly added 10.5 ml of an aqueous solution of cis-Pt(NH$_3$)(NO$_3$)$_2$.2H$_2$O containing 0.495 g/ml of platinum while stirring. A product slowly precipitated from the stirred solution but redissolved upon the addition of 10 ml of distilled water. An additional 2.1 ml of the platinum solution was added to provide a precipitated product of crosslinked nature. After filtration, washing and drying the thus produced composition of matter contained 33.68% platinum which calculates out to 86.0% of the carboxylic acid groups on the side chains of the poly-L-glutamic acid being complexed with the cis-[Pt(NH$_3$)$_2$]$^{++}$ moiety.

EXAMPLE X

In a preparation similar to that described in Example IX, 0.5 gram of the sodium salt of poly-L-glutamic acid was reacted with 0.312 gram of platinum in the form of the cis-Pt(NH$_3$)$_2$(NO$_3$)$_2$.2H$_2$O compound to provide a product containing 38.55% platinum. This equates to a reaction of 95.1% of the carboxylic acid units on the poly-L-glutamic acid with the cis-[Pt(NH$_3$)$_2$]$^{++}$ moiety.

EXAMPLE XI 0.857 gram of sodium carboxymethyl cellulose was dissolved in a mixture of 60 ml of water and 20 ml of dimethyl formamide. The containing flask was covered with aluminum foil and 9.6 ml of an aqueous solution of cis-Pt(NH$_3$)$_2$(NO$_3$)$_2$.2H$_2$O was added while stirring. After an hour product began to precipitate. Subsequently product was collected, vacuum filtered, washed with water and acetone and dried under vacuum. The thus produced product analyzed 24.8% platinum which equates to reaction of 88.2% of the free carboxylic acid groups of the carboxymethyl cellulose complexing with the cis-[Pt(NH$_3$)$_2$]$^{++}$ moiety.

TABLE I

| Treatment | No. Animals | Dosage mg Pt/kg | Median Day of Death | % ILS | Log$_{10}$ Change in Tumor Burden at End Rx |
|---|---|---|---|---|---|
| Negative Control(no treatment) | 20 | — | 10 | | |
| cis-Pt(DACH)(PGA)Complex | 3 | 96 | 16 | +60 | −4.1 |

TABLE I-continued

| Treatment | No. Animals | Dosage mg Pt/kg | Median Day of Death | Median % ILS | Log₁₀ Change in Tumor Burden at End Rx |
|---|---|---|---|---|---|
| | 3 | 48 | 17 | +70 | −4.8 |
| | 3 | 24 | 17 | +70 | −4.8 |
| | 3 | 12 | 14 | +40 | −2.7 |
| cis-Pt(DACH)(Bovine Serum Albumin)Complex | 3 | 96 | 14 | +40 | −2.7 |
| | 3 | 48 | 11 | +10 | −0.7 |
| | 3 | 24 | 11 | +10 | −0.7 |
| | 3 | 12 | 11 | +10 | −0.7 |
| cis-Pt(Biscyclohexylamine)₂(PGA) Complex | 3 | 96 | 13 | +30 | −2.1 |
| | 3 | 48 | 12 | +20 | −1.4 |
| | 3 | 24 | 11 | +10 | −0.7 |
| | 3 | 12 | 11 | +10 | −0.7 |
| cis-Pd(en)(PGA)Complex | 3 | 96 | Toxic | | — |
| | 3 | 48 | Toxic | | — |
| | 3 | 24 | 14 | +40 | −2.7 |
| | 3 | 12 | 10 | 0 | — |
| cis-Pd(NH₃)₂(PGA)Complex | 3 | 96 | Toxic | | |
| | 3 | 48 | 14 | +40 | −2.7 |
| | 3 | 24 | 10 | 0 | 0 |
| | 3 | 12 | 9 | −10 | +0.7 |
| cis-Pd(DACH)(PGA)Complex | 3 | 96 | Toxic | | |
| | 3 | 48 | Toxic | | |
| | 3 | 24 | 11 | +10 | −0.7 |
| | 3 | 12 | 10 | 0 | 0 |
| cis-Pt(DACH)(Dextran Sulfate) Complex | 3 | 6 | 22 | +100 | −6.7 |
| | 3 | 3 | 20 | +81 | −6.2 |
| | 3 | 1.5 | 18 | +63 | −4.8 |
| Negative Control(no treatment) | 20 | — | 11 | | |
| cis-Pt(NH₃)₂(PGA)Complex | 10 | 56 | Toxic | | |
| | 10 | 38 | 17 | +54 | −4.5 |
| | 10 | 25 | 16.5 | +50 | −4.2 |
| | 10 | 17 | 14 | +27 | −2.3 |
| | 10 | 11 | 13 | +18 | −1.5 |
| Positive Control(Cisplatin) | 10 | 5.2 | Toxic | | |
| | 10 | 3.5 | 18.5 | +68 | −5.7 |
| | 10 | 2.3 | 16.5 | +50 | −4.2 |
| Negative Control(no treatment) | 20 | — | 11 | | |

NOTE: Each test series is separated by a line.

EXAMPLE XII

The composition of matter as prepared in Example IX was tested for activity against ascites P388 leukemia in CDF1 female mice. At a non-toxic dose level of 30 mg/kg of mouse weight, administered interperitoneally as a single dose on the day following implantation of $10^6$ of tumor cells, the composition of matter of Example IX provided a 36% increase in life span and an approximate −3.0 log₁₀ change in tumor burden at the end of the test. Toxicity data on the composition of matter of Example IX derived from non-tumor bearing CDF1 female mice indicated $LD_{10}$, $LD_{50}$ and $LD_{90}$ of 68, 99 and 141 mg of platinum/kg of mouse respectively.

While in accordance with the provisions of the statute, there are described herein specific embodiments of the invention, those skilled in the art will understand that changes may be made in the form of the invention covered by the claims and that certain features of the invention may sometimes be used to advantage without a corresponding use of the other features.

The embodiments of the invention in which an exclusive property or privilege is claimed are defined as follows:

1. Lyophilized compositions of matter comprising initially water soluble anionic polysaccharides having anionic functional groups thereon and having at least part of the valence requirements of said anionic functional groups satisfied by a moiety of square planar coordination having the formula cis[MLL']++ wherein M is a metal species selected from the group of divalent platinum and divalent palladium and L and L' are selected from the group of ammonia and mono and difunctional primary amines.

2. Lyophilized compositions of matter as in claim 1 wherein the valence requirements of at least about 80% of said anionic functional groups are satisfied by said moiety of square planar coordination and said compositions of matter are essentially insoluble in water.

3. Lyophilized compositions of matter as in claim 1 wherein the valence requirements of less than about 80% of said anionic functional groups are satisfied by said moiety of square planar coordination and said compositions of matter are essentially soluble in water.

4. Lyophilized compositions of matter in accordance with claim 1 wherein said macromolecular entities have molecular weights of about 5,000 to about 60,000.

5. A lyophilized composition of matter in accordance with claim 3 where M is platinum, L and L' are the amino functions of 1,2-diaminocyclohexane and said macromolecular entity is dextran sulfate.

6. Lyophilized compositions of matter in accordance with claim 1 wherein said macromolecular entities are selected from the group consisting of chondroitin sulfate, dextran sulfate and carboxymethylcellulose.

* * * * *